US009320506B2

(12) United States Patent  (10) Patent No.: US 9,320,506 B2
Bertagnoli et al.  (45) Date of Patent: Apr. 26, 2016

(54) RETRACTOR SYSTEM FOR ANTERIOR CERVICAL SPINE SURGERY

(75) Inventors: Rudolf Bertagnoli, Vienna (AT); Steve Nowak, Traverse City, MI (US); Daniel K. Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 65 days.

(21) Appl. No.: 12/909,335

(22) Filed: Oct. 21, 2010

(65) Prior Publication Data

US 2011/0201897 A1  Aug. 18, 2011

Related U.S. Application Data

(60) Provisional application No. 61/253,685, filed on Oct. 21, 2009.

(51) Int. Cl.
*A61B 1/32* (2006.01)
*A61B 17/02* (2006.01)

(52) U.S. Cl.
CPC .................................. *A61B 17/0206* (2013.01)

(58) Field of Classification Search
CPC ........... A61B 17/0206; A61B 17/0218; A61B 17/0293
USPC ......... 600/201, 206, 208, 210, 211, 213–217, 600/219, 22, 225–229, 231, 234
See application file for complete search history.

(56) References Cited

U.S. PATENT DOCUMENTS

| 3,749,088 | A | * | 7/1973 | Kohlmann | 600/215 |
| 4,971,038 | A | | 11/1990 | Farley | |
| 5,902,233 | A | | 5/1999 | Farley et al. | |
| 5,931,777 | A | | 8/1999 | Sava | |
| 5,984,865 | A | | 11/1999 | Farley et al. | |
| 5,984,867 | A | * | 11/1999 | Deckman et al. | 600/232 |
| 6,468,207 | B1 | | 10/2002 | Fowler | |

(Continued)

FOREIGN PATENT DOCUMENTS

EP  1269922  1/2003
ES  2272170  4/2007

(Continued)

OTHER PUBLICATIONS

PCT International Search Report and Written Opinion, PCT/US2010/053510, mailed Dec. 27, 2010.

(Continued)

*Primary Examiner* — Jan Christopher Merene
*Assistant Examiner* — Atiya Mahmud
(74) *Attorney, Agent, or Firm* — McAndrews, Held & Malloy, Ltd.

(57) ABSTRACT

A retractor system includes a retractor blade that is securable to a portion of a patient's anatomy during a surgical procedure. The retractor system includes a manipulator that is releasably securable to the retractor blade for positioning and securing the retractor blade. The retractor system includes a flexible securement arm that movably secures the retractor blade to a frame, wherein a proximal end of the retractor blade is non-rigidly constrained. The securement arm is secured to the retractor blade proximate to one end of the securement arm, and is secured to a retractor frame proximate to another end of the securement arm.

17 Claims, 4 Drawing Sheets

(56) References Cited

U.S. PATENT DOCUMENTS

| | | | |
|---|---|---|---|
| 8,114,020 B2* | 2/2012 | Fricke et al. | 600/231 |
| 8,257,255 B2* | 9/2012 | Farley et al. | 600/213 |
| 2002/0026101 A1* | 2/2002 | Bookwalter et al. | 600/231 |
| 2002/0095071 A1* | 7/2002 | Farley | 600/231 |
| 2003/0069478 A1 | 4/2003 | Phillips et al. | |
| 2004/0129109 A1 | 7/2004 | Phillips et al. | |
| 2004/0199055 A1* | 10/2004 | Mulac et al. | 600/226 |
| 2004/0249388 A1 | 12/2004 | Michelson | |
| 2005/0113645 A1 | 5/2005 | Sharratt et al. | |
| 2005/0177028 A1* | 8/2005 | Royce et al. | 600/210 |
| 2005/0192484 A1* | 9/2005 | Sharratt et al. | 600/210 |
| 2006/0224044 A1* | 10/2006 | Marchek et al. | 600/233 |
| 2007/0270840 A1 | 11/2007 | Chin et al. | |
| 2008/0215081 A1* | 9/2008 | Hsueh et al. | 606/191 |
| 2009/0221876 A1 | 9/2009 | Cobb et al. | |

FOREIGN PATENT DOCUMENTS

| | | |
|---|---|---|
| FR | 2690067 | 10/1993 |
| FR | 2807313 | 10/2001 |
| GB | 1570499 | 7/1980 |

OTHER PUBLICATIONS

International Search Report and Written Opinion for International Patent Application Serial No. PCT/US2009/066425, mailed Feb. 10, 2010.

Non-Final Office Action, United States Patent and Trademark Office, U.S. Appl. No. 12/391,917, pp. 1-13, dated Jan. 1, 2011.

Patent Cooperation Treaty, International Bureau, Notification Concerning Transmittal of International Preliminary Report on Patentability, in International application No. PCT/US2010/053510, dated May 3, 2012. (8 pages).

\* cited by examiner

FIG.1

RETRACTOR SYSTEM FOR ANTERIOR CERVICAL SPINE SURGERY

CROSS-REFERENCE TO RELATED APPLICATION

This application claims priority to and the benefit of U.S. Provisional Application No. 61/253,685, entitled "Retract or System for Anterior Cervical Spine Surgery," filed Oct. 21, 2009, the entire content of which is incorporated herein by reference.

STATEMENT REGARDING FEDERALLY SPONSORED RESEARCH OR DEVELOPMENT

None.

BACKGROUND OF THE INVENTION

The present invention relates to surgical apparatus for retracting anatomy to provide exposure of an operative site, and more particularly relates to a retraction apparatus providing improved access to an operative site.

In surgical operations, retraction devices are used to properly access internal organs and bone structures. Retraction devices are generally designed to hold back the anatomy in the immediate area of the operative site to enable a surgeon to have both an optimal view of the site and a sufficiently-open area within which to work. During a surgical procedure, a surgeon will typically make an incision in a patient to access the sites of interest, such as an internal organ or organs, and/or bone structures, depending on the procedure. A retraction device may then be used to maintain clear access to the site of interest.

For example, during certain cervical spinal procedures, a surgeon may remove a disc and insert a bone graft or a synthetic disc. A retractor may be used to hold back tissue and allow a surgeon access to perform such a procedure. Ideally, such access would include room to manipulate the various surgical implements required, as well as good lighting and visibility. Further, it may be desirable for such access to allow for adjustability to accommodate different patients or procedures. During such a procedure, however, pounding of chisels, drilling, and preparation of the area site can result in movement of the spine, and affect the usefulness of the previously defined access site, or provide increased risk of injury relative to how the retractor blades are held in place.

In certain cervical spinal procedures, retractor blades may be held by hand. Such manual handling of retractor blades can increase the time and expense of a procedure, as well as including risk of injury should a blade slip or be mis-handled.

It is therefore one object of the present invention to provide a surgical retractor that provides improved access, and/or visibility, and/or adjustability, and/or maneuverability around a surgical site of interest.

BRIEF SUMMARY OF THE INVENTION

These and other objects of the invention are achieved in a retractor system having a retractor blade that is securable to a portion of a patient's anatomy during a surgical procedure. The retractor blade has a distal portion and a proximal portion. The distal portion is securable to a portion of a patient's anatomy during a surgical procedure. The retractor system includes a flexible securement arm adapted to movably secure the retractor blade to a frame. The flexible securement arm includes a first end adapted to be secured to a frame assembly and a second end adapted to be secured to the proximal portion of the retractor blade. The first and second ends are adapted to articulate in at least one direction with respect to each other, wherein a proximal end of the retractor blade is non-rigidly constrained.

In certain embodiments, the distal end of the retractor blade may include a tip having a sharp point, with the tip being adapted to be driven into a feature of a patient's anatomy. Additionally, the retractor system may further comprise a manipulator for positioning the retractor blade. The manipulator is releasably securable to the retractor blade. Further, the first and second ends of the flexible securement arm may be joined by a pivot. In certain embodiments, the pivot joining the first and second ends of the flexible securement arm includes a pin. Further, the pivot may allow rotation of the first and second ends of the flexible securement arm with respect to each other in one direction and substantially prevent rotation with respect to each other about any other axes.

In certain embodiments, the second end of the flexible securement arm and the proximal portion of the retractor blade are adapted to be joined such that the retractor blade may rotate about one axis with respect to the second end of the flexible securement arm, but is prevented from any substantial rotation about any other axes with respect to the second end of the flexible securement arm. For example, the proximal portion of the retractor blade may include a post having a retractor groove, and the second end of the flexible securement arm may include a ball configured to be accepted by the retractor groove. When the ball is accepted by the retractor groove, the retractor blade may rotate about one axis with respect to the second end of the flexible securement arm, but is prevented from any substantial rotation about any other axes with respect to the second end of the flexible securement arm. Further, the proximal portion of the retractor blade may include a handle. The post may extend from the handle, and also include a locking groove. The locking groove is located closer to the handle than the retractor groove. The locking groove is configured to accept the ball, and when the ball is accepted by the locking groove the retractor blade and the flexible securement arm are substantially prevented from rotating with respect to one another. Further still, the proximal portion of the retractor blade and the second end of the flexible securement arm may include cooperating serrated surfaces that restrict rotation of the retractor blade with respect to the second end of the flexible securement arm.

A method of providing access to a surgical site includes making an incision in a patient, introducing a retractor blade into the patient, positioning the retractor blade, securing a distal portion of the retractor blade inside the patient, providing a flexible securement arm having a first end adapted to be secured to a frame and a second end adapted to be secured to a proximal portion of the retractor blade, wherein the first and second ends are adapted to articulate in at least one direction with respect to each other, and securing the proximal portion of the retractor blade to a flexible securement arm, wherein the proximal end of the retractor blade is non-rigidly constrained by the flexible securement arm. The method may also include selecting one of a first and second location on the proximal portion of the retractor blade at which to secure the second end of the flexible securement arm. Securing the first end of the flexible securement arm to the first location on the proximal portion of the retractor blade allows the proximal portion of the retractor blade to rotate with respect to the first end, and securing the first end of the flexible securement arm to the second location on the proximal portion of the retractor blade restricts the retractor blade from rotating with respect to the first end.

DETAILED DESCRIPTION

Figure 1:
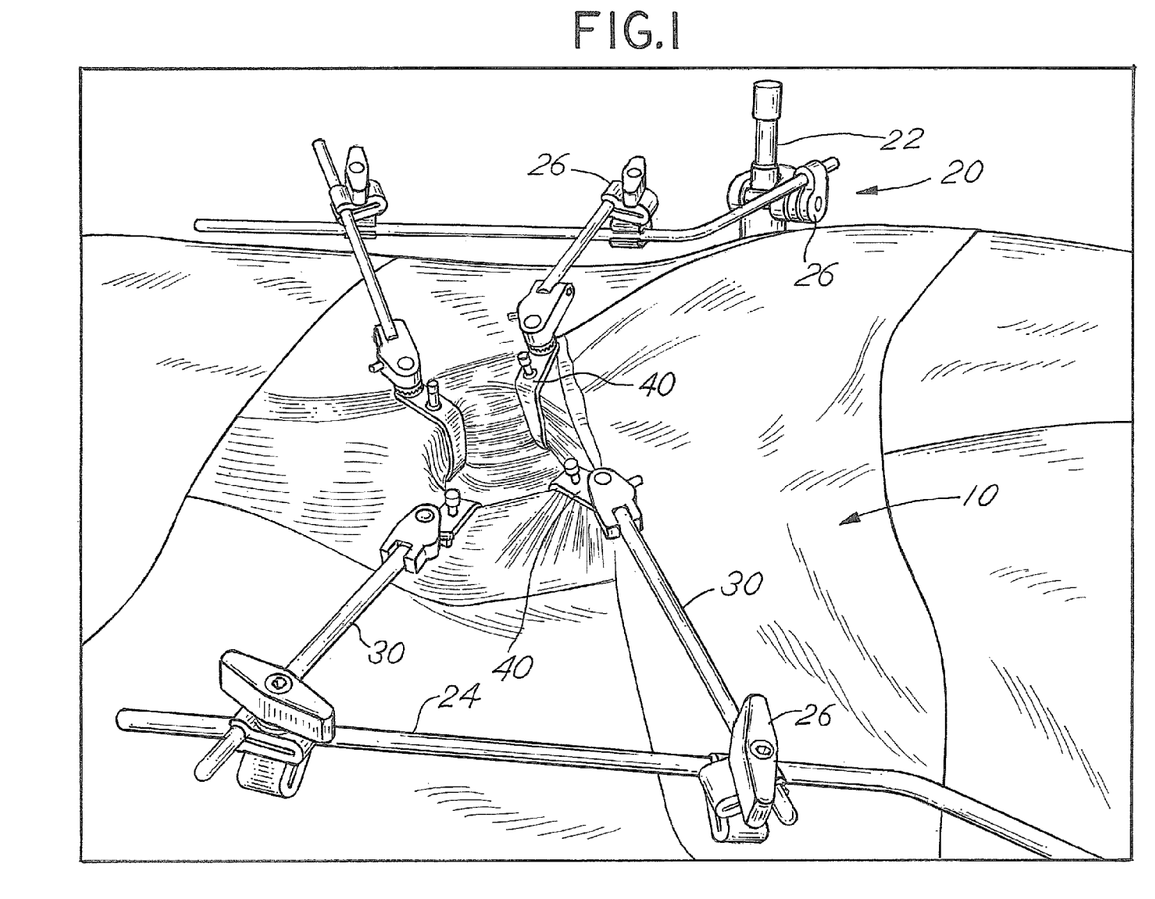
FIG. 1 provides a perspective view of a cervical spinal retractor system formed in accordance with an embodiment of the present invention.
Figure 2:
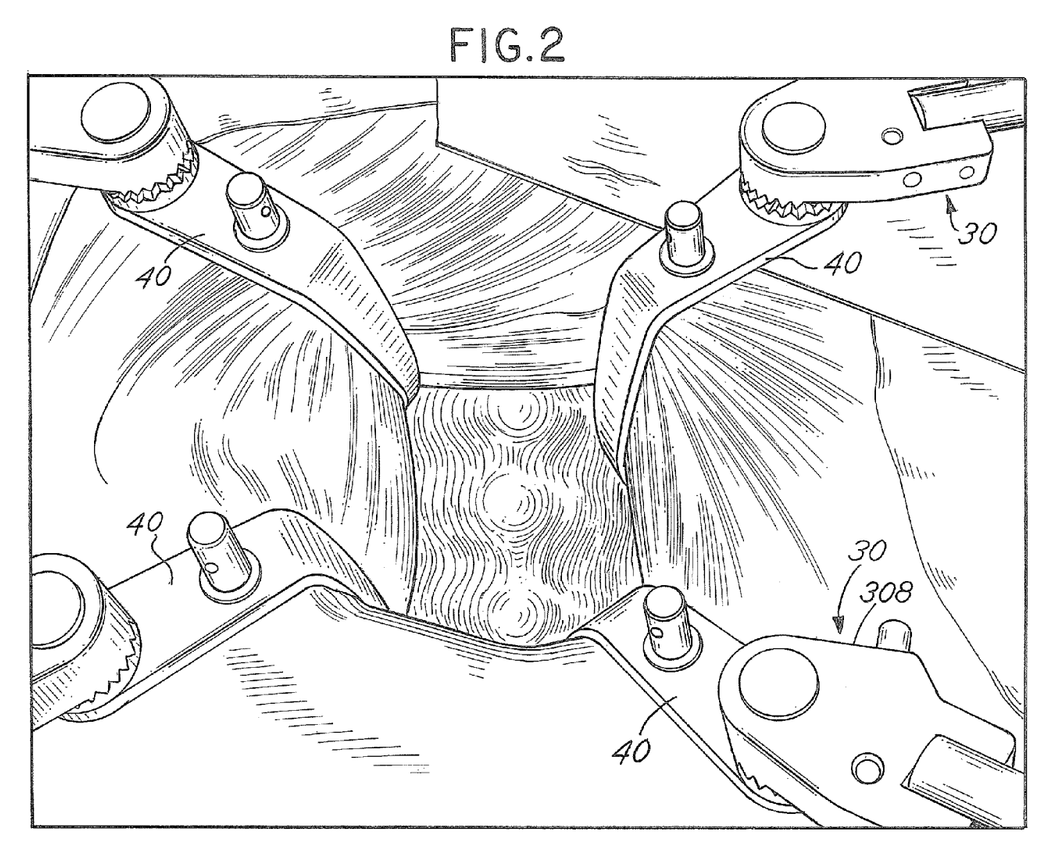
FIG. 2 provides an additional perspective view of a cervical spinal retractor system formed in accordance with an embodiment of the present invention.

FIGS. 1 and 2 illustrate an embodiment of a cervical spinal retractor system 10 formed in accordance with an embodiment of the present invention. The retractor system 10 includes a frame assembly 20, a jointed arm 30, and a plurality of retractor blades 40. The various components of the retractor system 10 may be made, for example, of stainless steel. While an embodiment particularly well adapted for anterior cervical spine surgery is discussed below and illustrated in the figures, the disclosed technology is not so limited and may be used for other procedures as well.

The frame assembly 20 includes a post 22, frame arms 24, and clamps 26. The post 22 is fixed to, for example, a rail and/or a hospital bed (not shown), and extends upward in a generally vertical direction. The post 22 provides a location to which to secure frame arms 24. In the illustrated embodiment, two posts 22 are secured on opposite sides of a hospital bed, with a frame arm 24 secured to each post 22 by a clamp 26. In the illustrated embodiment, the frame arms 24 are bent to extend toward the center of the hospital bed along a portion of their length. The frame arms 24 occupy a generally horizontal plane, and provide a location to which to mount other components of the retractor system 10, such as jointed arms 30 via additional clamps 26.

Figures 3, 4:
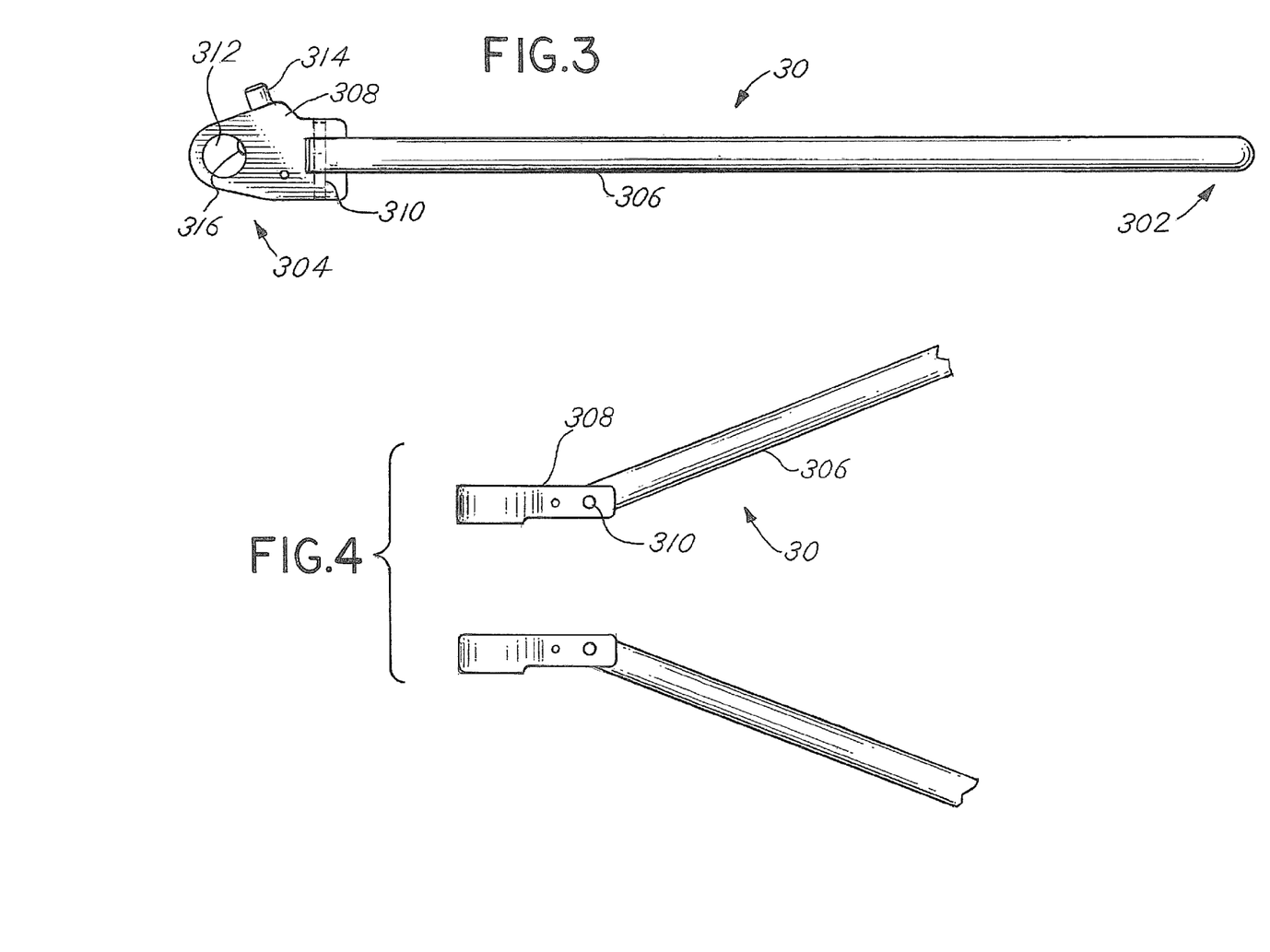
FIG. 3 illustrates a plan view of a jointed arm formed in accordance with an embodiment of the present invention.
FIG. 4 illustrates a side view of the jointed arm of FIG. 3.

FIG. 3 illustrates a plan view of a jointed arm 30 formed in accordance with an embodiment of the present invention, and FIG. 4 illustrates a side view of the jointed arm 30. The jointed arm 30 is adapted to provide for the non-rigid constraint of a proximal end of a retractor blade 40 when the retractor blade 40 is secured to the jointed arm 30. Put another way, the jointed arm 30 is adapted to provide at least some appreciable freedom of motion in at least one direction for the retractor blade 40 relative to the frame assembly 20, while preventing at least some motion of the retractor blade 40, allowing the proximal end of the retractor blade 40 some freedom of motion but maintaining the retractor blade 40 at or near a selected position to help maintain the desired access to an operative site. The illustrated jointed arm 30 is an example of a flexible arm used to secure a retractor blade 40 to the retractor frame assembly 20. While the illustrated embodiment utilizes a hinge in the jointed arm 30, other arrangements may also be used, such as, for example, a universal joint or a ball-and-socket arrangement, or as another example, a flexible portion located along the length of an arm.

In the illustrated embodiment, the jointed arm 30 includes a first end 302, a second end 304, an arm portion 306, a head 308, and a pivot 310 joining the arm 306 to the head 308. The first end 302 includes a portion adapted to be secured to the frame arm 24 with a clamp 26, and the second end 304 (the head 308 is located proximate to the second end 304) is adapted to be secured to a retractor blade 40.

The arm portion 306 is a generally straight, generally cylindrical member. In alternate embodiments, the arm portion 306 may be bent in one or more locations, or curved to accommodate different procedures or preferred shapes of access sites. The arm portion 306 is sized to be accepted by a clamp 26 proximate to the first end 302 of the jointed arm 30, whereby the first end 304 is substantially rigidly constrained and secured in place to the frame assembly 20.

The pivot 310 joins the arm 306 and the head 308, allowing the arm 306 and the head 308 to rotate relative to one another in one plane, but restricting their freedom of motion in other directions. For example, the pivot 310 may be a pin accepted by aligned holes in the arm 306 and 308. Again, as will be appreciated by one of skill in the art, alternative arrangements of flexible arms using mechanisms others than pivots may also be used in alternative embodiments.

The head 308 includes a securement hole 312, an actuating button 314, and a locking ball 316. In the illustrated embodiment, the securement hole 312, actuating button 314, and locking ball 316 cooperate to form a securement mechanism. Through the use of an internal mechanism (not shown), depressing the actuating button 314 allows increased freedom of movement of the locking ball 316, allowing a post or other structure to be inserted into or removed from the securement hole 312. Releasing the actuating button 314 constrains the locking ball 316 such that the locking ball 312 protrudes into the securement hole 312, acting to help secure any structure presently inserted into the securement hole. The securement hole 312 and locking ball 316 are sized and adapted to accept and secure a mounting feature of the retractor blade 40, as also discussed below. Thus, the head 308 may be secured to the retractor blade 40.

Figures 5, 6:
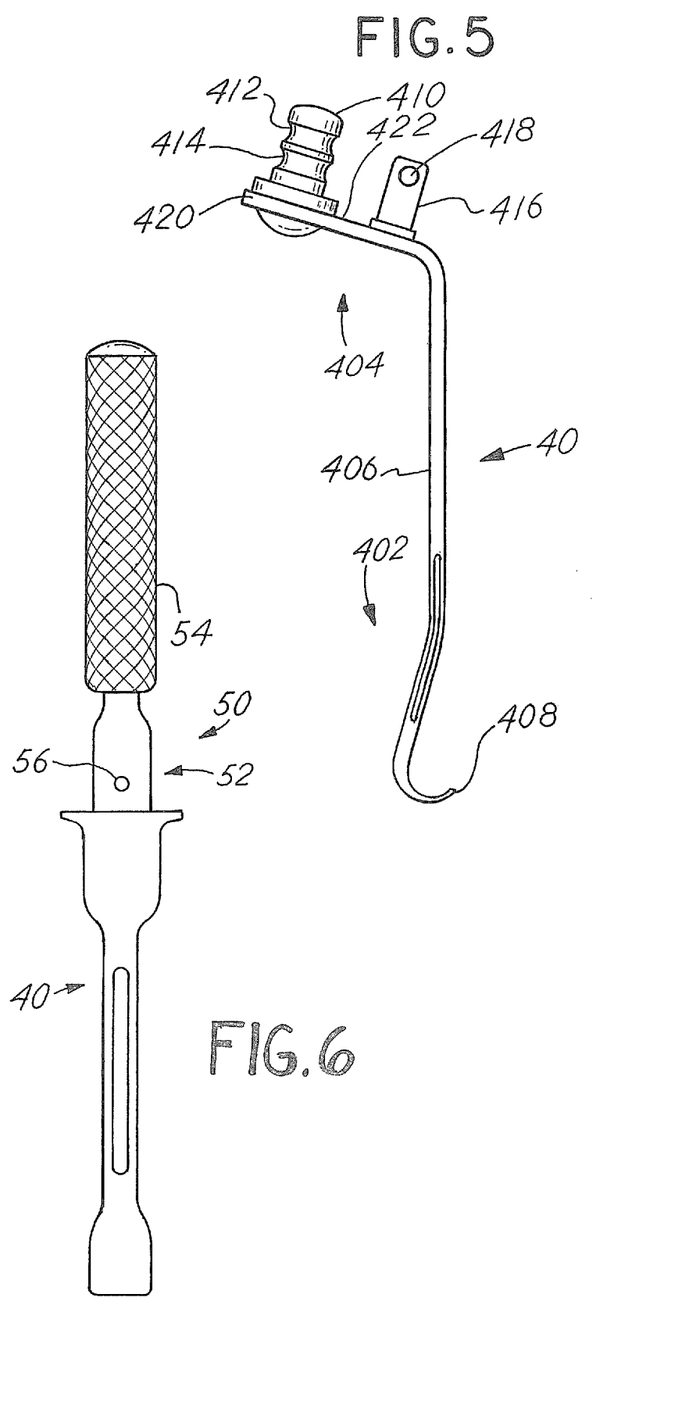
FIG. 5 illustrates an embodiment of a retractor blade formed in accordance with an embodiment of the present invention.
FIG. 6 illustrates a side view of a manipulator formed in accordance with an embodiment of the present invention.

FIG. 5 illustrates an embodiment of a retractor blade 40 formed in accordance with an embodiment of the present invention. The illustrated retractor blade 40 includes a distal end 402, a proximal end 404, a retracting surface 406, a tip 408, a handle 420, an arm securement feature 410, and a manipulator securement feature 416. The distal end 402 is the end of the retractor blade oriented more deeply inside the patient when the retractor blade 40 is positioned during a procedure, and the proximal end 404 is the end closer to a practitioner during a procedure.

In the embodiment illustrated in FIG. 5, the retractor blade 40 includes a tip 408 proximate to the distal end 402. The tip 408 is adapted to be securable to a part of a patient's spine. For example, in the illustrated embodiment, the tip 408 forms a sharp point that may be driven into a patient's spine. In alternate embodiments, other methods of securing the distal end of the retractor blade inside of a patient may be employed.

The retractor blade 40 includes a retracting portion 406 interposed between the tip 408 and the handle 420. In the illustrated embodiment, the handle 420 extends at an angle from the retracting portion 406, as shown in FIG. 5. The retracting portion 406 is sized and adapted to hold back tissue from a site of interest during a procedure. In certain embodiments, a retractor system may include a number of differently sized and/or shaped retractor blades to provide increased adaptability for different procedures and/or patients.

The handle 420 is located proximate to the proximal end 404 and provides a location or locations to grasp and/or secure the retractor blade 40. Located proximate to the handle 420 on the illustrated embodiment are the arm securement feature 410 and the manipulator securement feature 416.

The arm securement feature 410 is sized and adapted to provide a location for securement to the jointed arm 30. In the embodiment illustrated in FIG. 5, the arm securement feature 410 is sized and adapted to cooperate with the securement mechanism of the head 308 of the jointed arm 30. The illustrated arm securement feature 410 includes a generally cylindrically shaped post extending from the handle 420 including a first groove 412 and a second groove 414. The post and grooves are sized so that the securement feature 410 may pass freely through the securement hole 312 of the head 308 when the locking ball 316 of the head 308 is not constrained, but may be held in place when one of the grooves is aligned with the locking ball 316 and the locking ball 316 is constrained to protrude into the securement hole 312.

The first groove 412 provides a securement location for the securement mechanism of the head 308 slightly farther away from the handle 420 of the retractor blade 400. The first groove 412 is sized and adapted so that when the first groove 412 is aligned in the securement hole 310 and the locking ball 316 is constrained to protrude into the securement hole 310, the arm securement feature 410 is constrained from moving vertically with respect to the head 308. However, the first groove 412, securement hole 310, and locking ball 316 are sized and adapted such that the securement feature 410 may rotate with respect to the head 308. This provides an additional amount of allowed motion (in addition to the amount provided by the pivot 310) for the retractor blade 40 relative to the frame assembly 20 when the retractor blade 40 is secured to the jointed arm 30, which in turn is secured to the frame assembly 20.

In the embodiment illustrated in FIG. 5, the second groove 414 is located nearer to the handle 420. Further, the face 422 of the handle 420 as well as a face of the head 308 facing the handle 420 may have cooperating serrated surfaces (see FIG. 2) that restrict rotation of the securement feature 410 relative to the head 308 when the second groove 414 accepts the locking ball 316. Thus, by using either the first groove 412 or the second groove 414, a practitioner may alter the amount of freedom of movement of the retractor blade 40 relative to the head 308.

The manipulator securement feature 416 is sized and adapted to provide a location for securement of a manipulator for positioning the retractor blade 40. In the illustrated embodiments, the manipulator securement feature 416 is a generally cylindrical post extending from the handle 420 at a location slightly distal from the arm securement feature 410. The manipulator securement feature 416 includes a hole 418 sized and adapted to cooperate with a manipulator to secure the manipulator to the retractor blade 40.

FIG. 6 illustrates a side view of a manipulator 50 formed in accordance with an embodiment of the present invention. As illustrated in FIG. 6, the manipulator 50 is joined to a retractor blade 40. The manipulator 50 includes a mating portion 52 and a handle 54. The mating portion 50 is sized and adapted to cooperate with the manipulator securement feature 416 of the retractor blade 40. In the illustrated embodiment, the mating portion 52 includes a hole (not shown) that accepts the manipulator securement feature 416 and a ball 56 that cooperates with the hole 418 to secure the manipulator 50 to the retractor blade 40. The handle 54 is sized and adapted to be grasped by a practitioner. Once the retractor blade 40 is secured to the manipulator 50, the manipulator 50 provides for convenient manipulation and placement of the retractor blade 40. Once the retractor blade 40 is positioned as desired, the ball 56 may be actuated to release the manipulator 50 from the retractor blade 40.

To use the retractor system 10, the frame assembly 20 is first secured to the hospital bed. With the patient in place, an incision is made to provide access to the operative site of interest. A retractor blade 40 is then selected and secured to a manipulator 50. The retractor blade 40 is then inserted, distal end first, into the operative site of interest, and positioned as desired to retract tissue to provide access to the surgical site of interest. Once positioned as desired, the distal end of the retractor blade 40 may be secured in place by driving the tip 408 into, for example, a portion of a vertebra. Next, the manipulator 50 may be released from the retractor blade 40. The head 308 of a jointed arm 30 may now be secured to the arm securement feature 410 of the retractor blade 40, with the first end 302 of the jointed arm 30 secured to the frame assembly 20 with a clamp 26. Thus, the retractor blade 40 is secured at both its distal and proximal ends, removing the need for manual holding of the retractor blade during the procedure.

Further, while the jointed arm 30 generally maintains the retractor blade 40 in position, the motion permitted by the pivot 310 of the jointed arm and/or the interaction between the securement assembly and the first groove 412 (if the first groove 412 is utilized) allows some amount of "float" for the retractor blade 40 relative to the frame assembly 20 in the event of any pounding, chiseling, or other events that may cause portions of the anatomy or equipment to shift, helping to maintain a desired access shape as well as helping to reduce risk of any additional injury or trauma to the patient, as well as damage to any equipment, that may be caused by such a shift or movement. Next, additional retractor blades 40 may be added, positioned, and secured in place as desired. In the embodiment illustrated in FIGS. 1 and 2, four retractor blades have been used. Each of the retractor blades may be positioned independently of other retractor blades, in contrast to certain known systems that require, for example, paired blades to be located opposed to each other. Thus, the retractor system 10 provides for flexibility in the formation of the desired access site, as well as open access to the site of interest.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A retractor system for use with a frame during a surgical procedure, comprising:
   a retractor blade having a distal portion and a proximal portion, the distal portion configured for engagement with a portion of a patient's anatomy during a surgical procedure; and
   an adjustable securement assembly adapted to connect the retractor blade to the frame, the adjustable securement assembly having:
   (1) an arm, the arm having a first end and a second end, the first end adapted to be secured to the frame;
   (2) a mounting mechanism engageable with the arm to allow linear movement of the arm along a first axis relative to the frame, the mounting mechanism engageable with the arm to allow rotational movement of the arm about a second axis that is angularly disposed relative to the first axis; and
   (3) head assembly means for providing non-rigid constraint of the proximal portion of the retractor blade relative to the frame during the surgical procedure, said head assembly means located at the second end of the arm and being securable to the proximal portion of the retractor blade so as to allow rotation of the retractor blade with respect to the head assembly means about a third axis displaced from the second axis;

wherein the proximal portion of the retractor blade includes a handle and a post that extends from the handle;

wherein the post includes a retractor groove and a locking groove located closer to the handle than the retractor groove;

wherein the head assembly means includes a ball configured to be accepted by the retractor groove and the locking groove;

wherein the retractor groove is configured to accept the ball and permit rotation of the retractor blade about said third axis when the ball is accepted by the retractor groove; and wherein the locking groove is configured to accept the ball and prevent rotation of the retractor blade about the third axis when the ball is accepted by the locking groove.

2. The retractor system of claim 1, wherein said head assembly means includes a pivot mechanism; and wherein the second end is joined to the head assembly means by the pivot mechanism.

3. The retractor system of claim 2 wherein the pivot mechanism includes a pin defining a fourth axis of rotation for the retractor blade that is perpendicular to an axis disposed along a length of the arm.

4. The retractor system of claim 1, further comprising a manipulator for positioning the retractor blade, the manipulator being releasably securable to the proximal portion of the retractor blade.

5. The retractor system of claim 1, wherein the proximal portion of the retractor blade and the head assembly means include cooperating serrated surfaces that restrict rotation of the retractor blade about said third axis.

6. The retractor system of claim 1 wherein the distal portion of the retractor blade includes a tip having a sharp point, the tip being configured to be driven into a feature of a patient's anatomy.

7. The retractor system of claim 1, wherein the mounting mechanism includes a handle, the handle being configured for manipulation by a user, wherein manipulation of the handle allows the user to releasably secure the first end of the arm to permit movement along the first axis, and to releasably secure the first end of the arm to permit rotation about the second axis.

8. The retractor system of claim 1, wherein the mounting mechanism is engageable with the arm to permit rigid constraint of the arm relative to the frame.

9. A retractor system for use with a frame during a surgical procedure, comprising:

a retractor blade having a distal portion and a proximal portion, the distal portion securable to a portion of a patient's anatomy during a surgical procedure; and a jointed arm adapted to secure the retractor blade to the frame, the jointed arm having a first end adapted for securement to the frame and for enabling linear movement of the first end of the jointed arm along a first axis relative to the frame, wherein the first end of the jointed arm is configured to allow rotational movement of the first end of the jointed arm about a second axis angularly disposed to the first axis, wherein the jointed arm has a second end including head means for allowing said retractor blade to float relative to the frame during the surgical procedure, the head means being securable to the proximal portion of the retractor blade to allow the proximal portion of the retractor blade to rotate with respect to the head means about a third axis, and wherein the head means allows movement of the retractor blade relative to a fourth axis laterally disposed to the third axis;

wherein the proximal portion of the retractor blade includes a handle and a post that extends from the handle;

wherein the post includes a retractor groove and a locking groove located closer to the handle than the retractor groove;

wherein the head means of the jointed arm includes a ball configured to be accepted by the retractor groove and the locking groove;

wherein the retractor groove is configured to accept the ball and permit rotation of the retractor blade about said third axis when the ball is accepted by the retractor groove;

wherein the locking groove is configured to accept the ball to prevent rotation of the retractor blade about said third axis when the ball is accepted by the locking groove.

10. The retractor system of claim 9, wherein the first end of the jointed arm includes a mounting mechanism configured to allow movement of the first end of the jointed arm along the first axis and rotation of the first end of the jointed arm about the second axis.

11. The retractor system of claim 10, wherein the mounting mechanism includes a handle, the handle being configured for manipulation by a user; and wherein manipulation of the handle allows the user to releasably secure the first end of the jointed arm to permit movement along the first axis, and to releasably secure the first end of the jointed arm to permit rotation about the second axis.

12. The retractor system of claim 9 further comprising a manipulator for positioning the retractor blade, wherein the manipulator is releasably securable to the retractor blade.

13. The retractor system of claim 9, wherein the distal portion of the retractor blade includes a tip having a sharp point, the tip being configured to be driven into a feature of a patient's anatomy.

14. The retractor system of claim 9, wherein the head means includes a pivot connection, said pivot connection including a pin accepted by holes aligned in the head means and jointed arm.

15. The retractor system of claim 9, wherein the proximal portion of the retractor blade and the head means include cooperating serrated surfaces that restrict rotation of the retractor blade about said third axis.

16. A retractor system for use with a frame during a surgical procedure, comprising:

a retractor blade having a distal portion and a proximal portion, the distal portion configured for engagement with a portion of a patient's anatomy during a surgical procedure; and an adjustable securement assembly adapted to connect the retractor blade to the frame, the adjustable securement assembly having:

(1) an arm, the arm having a first end and a second end, the first end adapted to be secured to the frame;

(2) a mounting mechanism engageable with the arm to allow linear movement of the arm along a first axis relative to the frame, the mounting mechanism engageable with the arm to allow rotational movement of the arm about a second axis that is angularly disposed relative to the first axis; and (3) head assembly means for providing non-rigid constraint of the proximal portion of the retractor blade relative to the frame during the surgical procedure, said head assembly means located at the second end of the arm and being securable to the proximal portion of the retractor blade so as to allow rotation of the retractor blade with respect to the head assembly means about a third axis displaced from the second axis;

wherein the proximal portion of the retractor blade and the head assembly engage one another at a ball and groove connection, the ball and groove connection including a ball and a post with first and second grooves, wherein the first and second grooves are axially displaced from one another along a length of the post; and wherein the proximal portion of the retractor blade is freely rotatable about the third axis when the ball is engaged with the first groove and restrained from rotation about the third axis when the ball is moved into engagement with the second groove.

17. A retractor system for use with a frame during a surgical procedure, comprising:

a retractor blade having a distal portion and a proximal portion, the distal portion securable to a portion of a patient's anatomy during a surgical procedure; and a jointed arm adapted to secure the retractor blade to the frame, the jointed arm having a first end adapted for securement to the frame and for enabling linear movement of the first end of the jointed arm along a first axis relative to the frame, wherein the first end of the jointed arm is configured to allow rotational movement of the first end of the jointed arm about a second axis angularly disposed to the first axis, the jointed arm having a second end including head means for allowing said retractor blade to float relative to the frame during the surgical procedure, the head means being securable to the proximal portion of the retractor blade to allow rotation of the proximal portion of the retractor blade with respect to the head means about a third axis, and wherein the head means allows movement of the retractor blade relative to a fourth axis laterally disposed to the third axis;

wherein the proximal portion of the retractor blade and the head means engage one another at a ball and groove connection, the ball and groove connection including a ball and a post with first and second grooves, wherein the first and second grooves are axially displaced from one another along a length of the post; and wherein the proximal portion of the retractor blade is freely rotatable about the third axis when the ball is engaged with the first groove and restrained from rotation about the third axis when the ball is moved into engagement with the second groove.

* * * * *